United States Patent
Vanderlaan et al.

(10) Patent No.: US 6,500,481 B1
(45) Date of Patent: *Dec. 31, 2002

(54) BIOMEDICAL DEVICES WITH AMID-CONTAINING COATINGS

(75) Inventors: Douglas G. Vanderlaan; Ann-Marie Wong Meyers; David C. Turner; Joe M. Wood, all of Jacksonville, FL (US)

(73) Assignee: Johnson & Johnson Vision Care, Inc., Jacksonville, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/328,628

(22) Filed: Jun. 9, 1999

Related U.S. Application Data

(63) Continuation-in-part of application No. 09/096,148, filed on Jun. 11, 1998, now Pat. No. 6,087,415.

(51) Int. Cl.[7] .................................................. G02C 7/04
(52) U.S. Cl. ..................... 427/2.24; 427/164; 427/165; 428/411.1; 351/160 H; 523/106; 523/107; 523/108; 264/1.7
(58) Field of Search ................................ 427/2.24, 164, 427/165; 428/411.1; 351/160 H; 523/106, 107, 108; 264/1.7

(56) References Cited

U.S. PATENT DOCUMENTS

| | | |
|---|---|---|
| 3,900,672 A | 8/1975 | Hammond et al. ......... 428/334 |
| 4,143,949 A | 3/1979 | Chen |
| 4,191,596 A | 3/1980 | Dollman et al. ........... 148/6.27 |
| 4,217,038 A | 8/1980 | Letter et al. |
| 4,280,970 A | 7/1981 | Kesting |
| 4,293,642 A | 10/1981 | Beavav et al. .............. 430/534 |
| 4,312,575 A | 1/1982 | Peynan et al. |
| 4,373,009 A | 2/1983 | Alastaor .................. 428/424.4 |
| 4,379,893 A | 4/1983 | O'Malley et al. |
| 4,462,665 A | 7/1984 | Shah |
| 4,521,564 A | 6/1985 | Soloman et al. ............ 523/112 |
| 4,546,123 A | 10/1985 | Schafer et al. .............. 523/106 |
| 4,734,475 A | 3/1988 | Goldenberg et al. |
| 4,876,126 A | 10/1989 | Takemura et al. .......... 428/507 |
| 4,892,402 A | 1/1990 | Sawamoto et al. |
| 4,895,896 A | 1/1990 | Muller-Lieheim |
| 4,920,184 A | 4/1990 | Schafer et al. |
| 4,959,074 A | 9/1990 | Halpern et al. |
| 4,973,359 A | 11/1990 | Yamasoe ................. 106/19.13 |
| 4,973,493 A | 11/1990 | Guire ........................... 623/66 |
| 4,979,959 A | 12/1990 | Guire ........................... 623/66 |
| 5,002,582 A | 3/1991 | Guire et al. ................... 623/66 |
| 5,080,924 A | 1/1992 | Kamel et al. .................... 427/2 |
| 5,091,205 A | 2/1992 | Fan ................................ 427/2 |
| 5,108,776 A | 4/1992 | Goldberg et al. |
| 5,135,297 A | 8/1992 | Valint, Jr. |
| 5,135,516 A | 8/1992 | Sahatjin et al. ................. 435/6 |
| 5,217,492 A | 6/1993 | Guire et al. ................... 623/11 |
| 5,229,211 A | 7/1993 | Murayama et al. ...... 428/424.4 |
| 5,263,992 A | 11/1993 | Guire ........................... 623/66 |
| 5,272,012 A | 12/1993 | Opolski |
| 5,312,873 A | 5/1994 | Gregor et al. ............... 525/348 |
| 5,350,800 A | 9/1994 | Verhoven et al. ........... 523/112 |
| 5,397,848 A | 3/1995 | Yang et al. .................. 525/477 |
| 5,408,280 A | 4/1995 | von de Haegen et al. |
| 5,409,731 A | 4/1995 | Nakagawa et al. ......... 427/2.12 |
| 5,442,402 A | 6/1995 | Bowers et al. |
| 5,441,488 A | 8/1995 | Shimura et al. |
| 5,470,944 A | 11/1995 | Valint, Jr. et al. |
| 5,509,899 A | 4/1996 | Fan et al. |
| 5,578,675 A | 11/1996 | Mormile et al. ............. 524/589 |
| 5,584,882 A | 12/1996 | Yabushita et al. .............. 623/6 |
| 5,591,140 A | 1/1997 | Narayanan et al. |
| 5,614,035 A | 3/1997 | Nadkami |
| 5,620,738 A | 4/1997 | Fan et al. |
| 5,670,558 A | 9/1997 | Onishi et al. ................ 523/112 |
| 5,779,943 A | 7/1998 | Enns et al. |
| 5,805,264 A | 9/1998 | Janssen et al. ............... 523/108 |
| 5,858,653 A | 1/1999 | Duran et al. .................... 435/6 |
| 5,859,107 A | 1/1999 | Jones et al. .................. 524/406 |
| 5,879,436 A | 3/1999 | Kramer et al. ........... 106/14.42 |
| 5,910,518 A | 6/1999 | Nakada et al. |
| 5,997,517 A | 12/1999 | Whitbourne ................. 604/265 |
| 6,087,415 A | 7/2000 | Vanderlaan et al. |

FOREIGN PATENT DOCUMENTS

| | | |
|---|---|---|
| EP | 321 403 | 6/1989 |
| EP | 362 137 | 4/1990 |
| EP | 374 752 | 6/1990 |
| EP | 393 532 | 10/1990 |
| EP | 574 352 | 12/1993 |
| EP | 643 083 | 3/1995 |
| EP | 655 470 | 5/1995 |
| EP | 713 106 | 5/1996 |
| EP | 728487 | 8/1996 |
| EP | 747071 | 12/1996 |
| EP | 751 407 | 1/1997 |
| EP | 758 687 | 2/1997 |
| EP | 814 116 | 5/1997 |
| EP | 780419 | 6/1997 |
| EP | 963 761 | 12/1999 |
| WO | WO 89 09246 | 10/1989 |
| WO | WO 91/04283 | 4/1991 |
| WO | WO 92/09639 | 6/1992 |
| WO | WO 92/09650 | 6/1992 |
| WO | WO 93/00391 | 1/1993 |
| WO | WO 94/06485 | 3/1994 |
| WO | WO 95/04609 | 2/1995 |
| WO | WO 96/24392 | 8/1996 |
| WO | WO 97/18904 | 5/1997 |
| WO | WO 97 29160 | 8/1997 |
| WO | WO 98/33089 | 7/1998 |
| WO | WO 99/15917 | 4/1999 |

*Primary Examiner*—Peter Szekely

(57) ABSTRACT

The invention provides biomedical devices. In particular, the invention provides biomedical devices on the surfaces of which stable, hydrophilic, amide-containing coatings are formed.

31 Claims, No Drawings

BIOMEDICAL DEVICES WITH AMID-CONTAINING COATINGS

This is a Continuation-in-part (CIP) of prior application Ser. No. 09/096,148, filed Jun. 11, 1998, now U.S. Pat. No. 6,087,415.

FIELD OF THE INVENTION

This invention relates to biomedical devices. In particular, the invention provides biomedical devices on the surfaces of which stable, hydrophilic, amide-containing coatings are formed.

BACKGROUND OF THE INVENTION

Devices for use in and on the human body are well known. The chemical composition of the surfaces of such devices plays a pivotal role in dictating the overall efficacy of the devices. For example, many devices, including catheters, stents, lenses, and implants require biologically non-fouling surfaces, meaning that proteins, lipids, and cells will not adhere to the surfaces. Lenses also must be wettable by tear fluid in order to ensure wearer comfort. Additionally, providing such devices with an antimicrobial surface is advantageous.

A wide variety of methods have been developed to coat device surfaces to provide them with desired characteristics. However, the need still exists for a simple, efficient process that will provide a stable, hydrophilic coating.

DETAILED DESCRIPTION OF THE INVENTION AND PREFERRED EMBODIMENTS

The present invention provides a simple, economical process for producing devices with stable amide group-containing coatings including, without limitation, polyacrylamide coatings. In one embodiment, the invention provides a method for manufacturing biomedical devices comprising, consisting essentially of, and consisting of contacting at least one surface of a biomedical device, the surface comprising, consisting essentially of, and consisting of an effective amount of carboxyl groups with a coating-effective amount of an amine and a coupling effective amount of at least one coupling agent under conditions suitable to produce a stable, amide-containing coating on the surface. In another embodiment, the invention provides biomedical devices comprising, consisting essentially of, and consisting of a biomedical device at least one surface of the device having an amide-containing coating coupled thereto by at least one coupling agent.

By "biomedical device" is meant any device designed to be used while in or on either or both human tissue or fluid. Examples of such devices include, without limitation, stents, implants, catheters, and ophthalmic lenses. In a preferred embodiment, the biomedical device is an ophthalmic lens including, without limitation, contact or intraocular lenses. More preferably, the device is a contact lens.

It is an unexpected discovery of the invention that devices having carboxyl groups on their surfaces may be contacted with an amine to provide a hydrophilic, amide-containing coating for biomedical devices. It is another unexpected discovery of the invention that a high conversion of carboxyl groups to amide groups is obtained through the process of the invention. More specifically, a conversion of greater than about 80 percent, more preferably greater than about 90 percent, most preferably about 95 percent or greater, of the carboxyl groups to amide groups may be obtained. The carboxyl groups must be present in an amount effective to produce the desired number of amide groups when reacted with an amine. This amount is an amount of carboxyl groups per square centimeter of lens surface of about 0.65 to about 65 nMol/cm$^2$, preferably about 1 to about 50, more preferably about 1 to about 10 nMol/cm$^2$ of carboxyl groups.

In the process of the invention, a coating-effective amount of an amine is used, which amount is sufficient to convert the carboxyl groups present to the desired degree. The amine may be used as a part of a solution containing a solvent, such as an alcohol, tetrahydrofuran, or the like, or an aqueous solution. Preferably, an aqueous solution is used. The amount of amine in the solution may be about 5 volume percent, preferably about 1 volume percent, more preferably less than about 1 volume percent. The coatings produced by the process of the invention are stable, meaning that subjecting the coating to autoclaving, washing with a cleaning agent, and/or rinsing with a saline solution does not substantially alter the chemical properties of the coating.

A coupling effective amount of the coupling agent is used which amount is sufficient to enable to reaction of the carboxyl groups with the amine. The precise amount of coupling agent used will depend on the surface's chemistry as well as the amine and coupling agent selected. The amount of coupling agent used generally will be about 0.01 to about 25 weight percent, preferably about 0.1 to about 15, more preferably, about 0.1 to about 10 weight percent of the coating solution, or solvent, coupling agent and optional buffer. Suitable solvents are those capable of solubilizing both the amine and the coupling agent. Preferably, the process is carried out in a water, or aqueous, solution.

The contacting time typically may be about 1 to about 360 minutes, preferably 1 to about 240 minutes. The contacting temperature may be about 0 to about 95, preferably about 5 to about 80° C. The contacting, or reacting, of the amine and carboxyl groups may be carried out in any convenient manner.

Amines useful in the invention are any primary or secondary amines, their corresponding acid salts, amine-containing proteins, amine-containing antibiotics, and the like, and combinations thereof Examples of useful amines, proteins, and amine-containing antibiotics include, without limitation., ammonium chloride, glucosamine hydrochloride, dimethylamine hydrochloride, ethanolamine hydrochloride, diethanolamine hydrochloride, polyethylene glycol amines such as hexa(ethyleneglycol)-bis-amine, lactoferrin, lysozyme, albumin, casein, cytochrome C, immunoglobulins, avidin, heparin, polymyxin, and the like, and combinations thereof.

Coupling agents useful in the invention include any coupling agent capable of enabling the reaction of a carboxyl group with an amine group to form an amide. Useful suitable classes of coupling agents include, without limitation, dehydrating agents such as carbodiimides, acid halides of inorganic or organic acids, isocyanides, and the like, and combinations thereof Examples of suitable coupling agents include, without limitation, carbodimides, N,N'-carbonyldiimidazole, phosphoryl chloride, titanium tetrachloride, sulfuryl chloride fluoride, chlorosulfonyl isocyanate, phosphorus iodide, pyridinium salts of tributyl amine, phenyl dichlorophosphate, polyphosphate ester, chlorosilanes, and the like as well as mixtures of tributyl phosphorus and phenyl isocyanate, alkyl chloroformates and triethyl amine, 2-chloro-1,3,5-trinitrobenzene and pyridine, methyl sulfuryl chloride and diethyl amine, and triphenylphosphine, carbon tetrachloride and triethyl amine. Preferred coupling agents are carbodiimides. More preferred are 1-ethyl-3-(3-dimethylaminopropyl) carbodiimide and dicyclohexyl carbodiimide.

The devices used for purposes of the invention may be made of one or more carboxyl functional hydrophilic polymers. Alternatively, one or more surfaces of a device may be coated with one or more carboxyl functional polymers. Thus, in yet another embodiment, the invention provides a method for manufacturing biomedical devices comprising, consisting essentially of, and consisting of coating at least one surface of a device with one or more carboxyl functional polymers, subsequently contacting the at least one surface with a coating-effective amount of an amine and a coupling effective amount of at least one coupling agent under conditions suitable to produce a stable, amide-containing coating on the surface.

Examples of suitable carboxyl functional hydrophilic polymers include, without limitation, poly(acrylic acid), poly(methacrylic acid), poly(maleic acid), poly(itaconic acid), block or random copolymers of (meth)acrylic acid, acrylic acid, maleic acid, itaconic acid with any reactive vinyl monomer, carboxymethylated polymers, such as carboxymethylcellulose, and the like, and mixtures thereof. Preferably, the carboxyl functional hydrophilic polymer is poly(acrylic acid) or poly(methacrylic acid). More preferably, poly(acrylic acid) is used.

The carboxyl functional polymers may be of any molecular weight. Preferably, the polymers are of a relatively high molecular weight, or about 10,000 to 10,000,000 more preferably about 50,000 to about 4,000,000 g/mole, most preferably about 100,000 to about 1,000,000 g/mole.

Suitable surfaces for coating with a carboxyl functional polymer are any surfaces with hydroxyl groups, amino groups, or mixtures thereof Preferably, the surface is made of a silicone elastomer, silicone-containing macromers including, without limitation, those disclosed in U.S. Pat. Nos. 5,371,147, 5,314,960, and 5,057,578 incorporated in their entireties herein by reference, hydrogel, or silicone-containing hydrogel. More preferably, the surface is a siloxane, or contains a siloxane functionality, including, without limitation, polydimethyl siloxane macromers, methacryloxypropyl polyalkyl siloxanes, and mixtures thereof, silicone hydrogel or a hydrogel, such as etafilcon.

If the surface material to be coated does not contain the requisite hydroxyl or amine groups, such groups may be incorporated into the surface material. For example, hydroxyl groups may be incorporated by addition of one or more hydroxyl-containing monomers into the polymers used to form the surface. Examples of such hydroxyl containing monomers include, without limitation, mono(meth)acrylates of ethylene glycol, propylene glycol, glycerol, tetraethylene glycol, and the like. Amino groups may be incorporated using, without limitation, (meth)acrylates of aminoalcohols such as aminoethanol, tert-butylaminoethanol, or (meth) acrylamides of diamines such as bisaminopropane.

Alternatively, amine or hydroxyl functional, silicone-containing monomers or macromers may be used to incorporate the hydroxyl or amino functionalities into the surface. Suitable hydroxyl containing macromers include, without limitation, silicone containing linear or branched hydroxyalkylamine functional monomers of the structure:

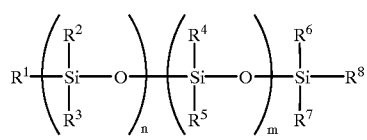

wherein: n is 0 to 500, m is 0 to 500, and n+m=10 to 500, preferably 20 to 250; $R^2$, $R^4$, $R^5$, $R^6$, and $R^7$ are each independently a substituted or, preferably, unsubstituted monovalent alkyl of 1 to 10 carbon atoms or a substituted or, preferably, unsubstituted aryl group, suitable substituents for which include alcohol, ester, amine, ketone, carboxylic acid, or ether groups; $R^1$, $R^3$, and $R^8$ are each independently a substituted or, preferably unsubstituted monovalent alkyl of 1 to 30 carbon atoms or a substituted or, preferably, unsubstituted aryl group suitable substituents for which are alcohol, ester, amine, ketone, carboxylic acid, or ether groups, and at least one of $R^1$, $R^3$, and $R^8$ is of the formula:

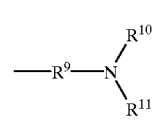

wherein $R^9$ is any group capable of linking N to Si, including without limitation, a linear or branched divalent alkyl of 1 to about 10 carbon atoms or an ether group, $R^{10}$ and $R^{11}$ are each independently H, a substituted or unsubstituted monovalent alkyl of 1 to 5 carbon atoms, a substituted or unsubstituted aryl group, suitable substituents for which are substituted with alcohol, ester, amine, ketone, carboxylic acid, or ether groups, or the structure:

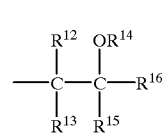

wherein $R^{14}$ is H or a monovalent (meth)acryloyl, styryl, vinyl, allyl, or N-vinyl lactam polymerizable group and preferably H or methacryloyl; $R^{16}$ is H, a monovalent substituted or unsubstituted alkyl group of 1 to 6 carbon atoms, a substituted or unsubstituted aryl group, suitable substituents for which are alcohol, ester, amine, ketone, carboxylic acid, or ether groups, or a (meth)acrylate, styryl, vinyl, allyl, or N-vinyl lactam polymerizable group and preferably is an alkyl group of 1 to 6 carbon atoms substituted with an alcohol or is a methacrylate; $R^{12}$, $R^{13}$, and $R^{15}$ are independently H, a substituted or unsubstituted monovalent alkyl of 1 to 6 carbon atoms, a substituted or unsubstituted aryl, suitable substituents for which include alcohol, ester, amine, ketone, carboxylic acid, or ether groups, or $R^{12}$ and $R^{15}$ or $R^{13}$ and $R^{15}$ form a ring structure with the proviso that at least some of the structure II groups on the monomer are polymerizable groups. Preferably, $R^{12}$, $R^{13}$, and $R^{15}$ are H.

Silicone-containing polymers useful in the present invention may also be copolymers incorporating one or more hydrophilic monomers. The hydrophilic monomers used to make the hydrogel used in the invention may be any of the known monomers useful for hydrogel formation.

Preferred hydrophilic monomers used in forming the carboxyl functional hydrophilic containing surfaces useful in the process of this invention are acrylic or vinylic-containing. Acrylic-containing monomers contain the group ($CH_2$=CRCOX) wherein R is H or $CH_3$, and X is O or N. Examples of such monomers include, without limitation, N,N-dimethylacrylamide, 2-hydroxyethyl methacrylate, glycerol methacrylate, 2-hydroxy ethyl methacrylamide, polyethylene glycol monomethacrylate, methacrylic acid, acrylic acid, and the like.

Vinylic-containing monomers refers to monomers containing the group (—CH=$CH_2$). Examples of such monomers include, without limitation, N-vinyl lactams, such as N-vinyl pyrrolidone, and N-vinyl-N-methyl acetamide, N-vinyl-N-ethyl acetamide, N-vinyl-N-ethyl formamide, N-vinyl formamide and the like. Preferably, the monomer is N-vinyl pyrrolidone.

Other hydrophilic monomers that may be employed in forming the surfaces of the invention include, without limitation, polyoxyethylene polyols having one or more terminal hydroxyl groups replaced with a functional group containing a polymerizable double bond. Examples include, without limitation, polyethylene glycol, ethoxylated alkyl glucoside, and ethoxylated bisphenol A reacted with one or more equivalents of an end-capping group such as isocyanatoethyl metliacrylate, methacrylic anhydride, methacryloyl chloride, vinylbenzoyl chloride, or the like to produce a polyethylene polyol having one or more terminal, polymerizable, olefinic groups bonded to the polyethylene polyol through linking moieties such as carbamate or ester groups.

Additional exemplary hydrophilic monomers are disclosed in U.S. Pat. Nos. 5,070,215 and 4,910,277, which are incorporated herein in their entireties by reference. Preferred hydrophilic monomers are N,N-dimethylacrylamide, 2-hydroxyethyl methacrylate, glycerol methacrylate, 2-hydroxyethyl methacrylamide, N-vinyl pyrrolidone, polyethylene glycol monomethacrylate, and (meth)acrylic acid. Most preferably, N,N-dimethylacrylamide is used.

The surface to be coated with the carboxyl functional hydrophilic polymer is contacted with the polymer and at least one coupling, agent in any convenient manner. For example, the device may be placed in a solution of polymer and solvent into which the coupling agent is added. As an alternative, and preferably, the device surface may first be contacted with one of the coupling agent or polymer and then contacted with the other. Most preferably, the surface is first contacted by any convenient method with the coupling agent for a period of about 0.5 to about 60 minutes, preferably for about 1 to about 30 minutes. For example, the surface may be soaked in a coupling agent solution. Subsequently, the surface is contacted with the carboxyl functional hydrophilic polymer solution for a period of about 1 to about 1000 minutes, preferably about 5 to about 200 minutes.

Suitable solvents for use in the invention are those that are capable of solubilizing both the carboxyl-functional polymer and the coupling agent. Preferably, the coating process is carried out in a water or aqueous solution, which solution preferably contains buffers and salts. The carbodiimide 1-ethyl-3-(3-dimethylaminopropyl)carbodiimide ("EDC") is effective in aqueous solutions and, thus, is a most preferred coupling agent.

The coupling agents may be used alone or in combination with agents capable of stabilizing any reactive intermediate formed. For example, EDC may be used with N-hydroxysuccinimide as a stabilizer. Additionally, it may be necessary to adjust the solution pH in order to optimize ester or amide linkage formation. Preferably, the pH is adjusted to from about 2.0 to about 8.0, more preferably from about 4.5 to about 5.0.

A coupling effective amount of the coupling agent is used which amount is sufficient to couple the polymer to the device surface. The precise amount of coupling agent used will depend on the surface's chemistry as well as the polymer and coupling agent selected. Generally, about 0.01 to about 10 weight percent, preferably about 0.01 to about 5.0, more preferably, about 0.01 to about 1 weight percent of the coating solution is used. By coating solution is meant the polymer with one or more of the solvent, coupling agent, and buffer. Typically, the amount of coating solution used per lens will be about 0.1 to about 100 g, preferably about 0.5 to about 50 grams, more preferably about 1 to about 10 g per lens.

A coating effective amount of carboxyl functional hydrophilic polymer is used meaning an amount sufficient to coat the surface to the desired degree. Generally, the amount of polymer used is about 0.001 to about 100, preferably about 0.01 to about 50, more preferably, about 0.01 to about 10 weight percent of the coating solution.

Temperature and pressure are not critical to the process, which may be conveniently carried out at room temperature and pressure. However, in a preferred embodiment, a temperature of about 30 to about 80° C. is used. The contact time used will be a length of time sufficient to coat the surface to the extent desired. If the surface is being contacted with a coupling agent-polymer solution, generally, contact times will be from about 1 minute to about 24 hours, preferably from about 1 to about 120 minutes, more preferably from about 1 minute to about 60 minutes.

If the surface is first treated with only the coupling agent, the contacting time will be about 1 to about 120, preferably 2 to about 60 minutes. The surface then is contacted with the polymer-solvent solution as described above.

One ordinarily skilled in the art will recognize that the formulation for producing the surface to be coated by the method of the invention may contain other monomers and additives. For example, ultra-violet absorbing monomers, reactive tints, processing aids, and the like may be used.

Following contacting, the surface may be washed with water or buffered saline solution to remove unreacted polymer, coupling agent, solvent, and byproducts. Optionally, the coated surface may be heated in water to extract residual coating, coupling agent, and byproducts and to ensure the break down of any coupling agent—stabilizer complexes that may have formed.

The invention will be further clarified by a consideration of the following, non-limiting examples.

EXAMPLES

Example 1

A soft contact lens made of poly(2-hydroxyethylmethacrylate) crosslinked with ethyleneglycol dimethacrylate, known under the USAN name of polymacon, was swollen in saline and then placed into a 3.0 g of a solution of 1.0% poly(acrylic acid sodium salt) (60,000 MW) and 1.4% concentrated HCl (35% by wt in water). 9.0 mg of EDC were then added and the lens was rolled for 1.0 hr at room temperature, the lens was removed from the solution and rinsed x5 with a borate buffered saline solution. The borate buffered solution was prepared by dissolving 8.48 g NaCl, 9.26 g boric acid, and 1.0 g sodium borate and 1.0 g of EDTA per liter of water. The lens was then placed into 2.0 g of a solution of 5.0% $NH_4Cl$ to which 0.20 g EDC were added. After 1 hr, the lens was removed and rinsed x5 with borate buffered saline solution.

The lens' surface was examined by atomic force microscopy ("AFM") using a 0.06 N/m $SiN_4$ cantilever imaging in solution. Imaging force was minimized before data was acquired and was typically <10 nN. Images were 50×50 μm areas, within the lens' optical zone, on the anterior surface of the lens. Two images were taken of the lens after its immersion in the borate buffered saline solution and two after the subsequent immersion in 0.1% HCl (pH 1.7). The lens was then returned to borate buffered saline and re-analyzed. The AFM experiment was also conducted on PAA-coated polymacon lenses that were not reacted with $NH_4Cl$.

The results are shown in Table 1. Roughness values are for 25×25 μm area. Because the surface roughness of a PAA coating correlates with coating thickness, the results demonstrate that the PAA-coated lenses unreacted with $NH_4Cl$ are reduced in thickness hen treated with acid, presumably because the carboxylic acid groups become protonated. The $NH_4Cl$ reacted lenses are substantially undiminished in thickness consistent with essentially complete conversion of the surface carboxylate groups to amide groups.

TABLE 1

| Sample | Root Mean Square Mean Roughness (nm) | Root Mean Square Median Roughness (nm) |
| --- | --- | --- |
| PAA Coated Lens | 140 | 145 |
| PAA Coated Lens; Acid | 15.9 | 14.7 |
| PAA Coated Lens; Saline | 142 | 140 |
| $NH_4Cl$ Reacted Lens | 49 | 50 |
| $NH_4Cl$ Reacted Lens; Acid | 88 | 88 |
| $N_4Cl$ Reacted Lens; Saline | 57 | 58 |

Example 2

The lenses of Example 1 were analyzed by X-ray photoelectron spectroscopy (XPS). The results shown in Table 2 demonstrate that the amount of nitrogen is increased and the amount of oxygen decreased on the $NH_4Cl$ reacted lenses.

TABLE 2

| Lens | Carbon | Nitrogen | Oxygen |
| --- | --- | --- | --- |
| Uncoated | 62.7 | 0.5 | 31.3 |
| PAA Coated | 48.2 | 0.7 | 36.1 |
| PAA Coated; Reacted With $NH_4Cl$ | 68 | 13.8 | 17.5 |

Example 3

Fifty soft, silicone hydrogel lenses were made from copolymerizing a blend of silicone-containing macromer and monomers (methacryloxypropyltris (trimethylsilyloxysilane) ("URIS"), N,N-dimethylacrylamide ("DMA"), tetraethyleneglycol dimethacrylate, and 2-hydroxyethylmethacrylate). The lenses had a water content of approximately 31% and a hydroxyl content of approximately 0.5 mmoles OH/g polymer. The lenses were soaked in a solution of 0.5% EDC for 10 minutes. The lenses were transferred into 150 mL of a solution of 250,000 MW poly(acrylic acid). After 4 h, the lenses were removed and rinsed ×5 with borate buffered saline solution.

Forty-four of the lenses were placed in 100 mL of a solution of 100 mg bovine colostrum lactoferrin and 0.60 g EDC in 0.10 molar (pH 6.0) 2-(N- morpholino) ethanesulfonic acid ("MES ") buffer. After 16 hr at room temperature, the lactoferrin coated lenses were rinsed ×5 with borate buffered saline solution.

Thirty-nine lenses were placed in 100 g of a solution of 5.0% $NH_4Cl$. 10 g EDC was then added. After 3 hr at room temperature, the lenses were removed and rinsed ×5 with borate buffered saline solution.

Two each of lenses coated with PAA alone, PAA-lactoferrin, and PAA-lactoferrin-$NH_4Cl$ were treated with rhodamine to visualize free carboxyl groups according to the following method. Two lenses were placed into 4.0 mL (pH 6.0) MES buffer. 200 μg tetramethylrhodamine cadaverine (40 μl of a 5 mg/mL solution) and 60 mg EDC were added. The vial was shaken and allowed to react at room temperature for 2 hr. The lenses were then rinsed ×3 with borate buffered saline solution and ×1 with a 1:1 blend of water and isopiopanol and then placed into borate buffered saline. The PAA only coated lenses had a dark red color; the PAA-lactoferrin lenses had a much lighter red color; the PAA-lactoferrin-$NH_4Cl$ lenses had no red color.

Example 4

Two soft, hydrogel contact lenses made from lenefilcon A, a hydrogel made from a crosslinked copolymer of hydroxyethylmethacrylate and glycerol methacrylate, and coated with 60,000 MW PAA were placed into a solution of 0.25 g glucosamine hydrochloride in 4.75 g water. 0.5 g EDC were added and after 1 hr, the lenses were rinsed ×5 with fresh borate-buffered saline solution. The lenses were treated with rhodamine using the procedure of Example 3. The lenses exhibited very little red color compared to identical PAA coated lenses untreated with gluocosamine.

Example 5

Two soft, hydrogel contact lenses made from lenefilcon A and coated with 60,000 MW PAA were placed into a solution of 0.25 g dimethylamine hydrochloride in 4.75 g water. 0.5 g EDC were added and after 1 hr, the lenses were rinsed ×5 with fresh borate-buffered saline solution. The lenses were treated with rhodamine using the procedure of Example 3. The lenses exhibited very little red color compared to identical PAA coated lenses untreated with dimethylamine hydrochloride.

Example 6

Soft, hydrogel contact lenses made by the procedure of Example 3 were coated with 250,000 MW PAA as follows. 100 lenses were placed in 200 mL of a 3% (w/w) PAA solution in borate buffered saline. 0.6 g EDC were added and after 1 hr the lenses were rinsed ×5 with fresh borate buffered saline solution. Four of these PAA-coated lenses were immersed in 8.5 mL of pH 6.05 MES buffer containing 0.47 g of hexa(ethylene glycol)-bis-amine. 0.42 g EDC were added and after 7 hr at room temperature, the lenses were rinsed ×4 with fresh borate buffered saline solution. The lenses were treated with rhodamine using the procedure of Example 3. The lenses exhibited less red color compared to identical PAA coated lenses untreated with hexa(ethylene glycol)-bis-amine.

Example 7

One hundred twenty soft contact lenses made from etafilcon A were placed into 120 mL of 300 mg bovine colostrum lactoferin in deionized ("DI") water into which 1.80 g EDC were added. After 24 h of slow stirring at room temperature these lactoferrin-coated lenses were rinsed ×10 with fresh borate buffered saline solution. Approximately 58 µg of lactoferrin were found on each lens by hydrolysis with 6 N HCl and derivitization with phenyl thioisocyanate followed by HPLC indicating that the lactoferrin amine groups reacted with the surface's carboxyl groups.

Example 8

Forty etafilcon A lenses were placed into 13.7 g of a solution Of 3.0% 250,000 MW PAA in 160 mL fresh borate buffered saline solution to which 0.48 g EDC were added. After 1 hr of rolling at room temperature, the lenses were rinsed ×10 in fresh borate buffered saline solution.

The lenses were then placed into 40 mL of a solution of 100 mg bovine colostrum lactoferrin in 0.10 molar pH 4.7 MES buffer into which 0.60 g EDC were added. After 19 h of slow stirring at room temperature, these lactoferrin-coated lenses were rinsed ×10 with fresh borate buffered saline solution. Approximately 660 µg of lactoferrin were found on each lens per HPLC.

Example 9

Forty soft, silicone hydrogel lenses (made as disclosed in Example 6) with a water content of approximately 31% and a hydroxyl content of about 0.5 mmoles OH/g polymer were placed into 3% solution of 250,00 MW PAA in borate buffered saline solution to which 0.48 g EDC were added. After 1 hr of rolling at room temperature, the lenses were rinsed ×10 in fresh borate buffered saline solution.

The lenses were then placed into 40 mL of a solution of 100 mg bovine colostrum lactoferrin in 0.10 molar pH 4.7 MES buffer into which 0.60 g EDC were added. After 65 hr of stirring at room temperature, these lactoferrin-coated lenses were rinsed ×10 with fresh borate buffered saline solution. Approximately 119 µg of lactoferrin were found on each lens by hydrolysis with 6 N HCl and derivitization with phenyl thioisocyanate followed by HPLC.

Example 10

Twenty soft, hydrogel contact lenses made from lenefilcon A and coated with 250,000 MW PAA were placed into a solution of 50 mg bovine colostrum lactoferrin in 20 mL DI water into which 0.30 g EDC were added. After 22 hr rolling at room temperature, these lenses were rinsed ×10 with fresh borate buffered saline solution. Approximately 37 µg of lactoferrin were found on each lens by hydrolysis with 6 N HCl and derivitization with phenyl thioisocyanate followed by HPLC.

Example 11

One hundred fifteen soft, hydrogel contact lenses made from lenefilcon A were soaked in a solution of 0.5% EDC in DI water for 10 min and then transferred into 230 mL of a solution of 1.5% 60,000 MW poly(acrylic acid sodium salt) and 1.4 % concentrated (35% by wt in water) HCl in fresh borate buffered saline solution. After 1 hr rolling at room temperature, these PAA-coated lenses were rinsed ×5 with fresh borate buffered saline solution. The lenses were treated with rhodamine following the procedure of Example 3. The lenses had a dark pink color and advancing contact angles of 34 degrees with a receding angle of 36 degrees with buffered saline.

Seventy of the lenses were again soaked in a 0.5% EDC solution in DI water for 10 min. and then transferred into a 40 mL solution of 100 mg bovine colostrum lactoferrin in 0.10 molar pH 6.0 MES buffer. After 1 hr of rolling at room temperature these lactoferrin-coated lenses were treated with rhodamine following the procedure of Example 3. The lenses were similar in color to the PAA-coated lenses. The lenses had an advancing contact angle of 57 degrees with a receding angle of 49 degrees with buffered saline. The change in contact angles indicates modification of the surface by the lactoferrin. The pink color indicates the presence of unreacted carboxyl groups.

Thirty-five of the lenses were then soaked in a solution of 10% EDC in DI water for 10 min and placed into 3.5 g of a solution of 5.0% NH$_4$Cl in DI water. After 1 hour of rolling at room temperature, the lenses were rinsed ×5 with fresh borate buffered saline solution. Approximately 15 µg of lactoferrin were found on each lens by hydrolysis with 6 N HCl and derivitization with phenyl thioisocyanate followed by HPLC. The lenses were treated with rhodamine following the procedure of Example 3 and found to have much less red color as compared to identical PAA-coated lenses that were not treated with NH$_4$Cl. These lenses also had an advancing contact angle of 61 degrees and a receding angle of 51 degrees with buffered saline. The results indicate that the residual carboxyl groups have been reacted in the second amidification.

Example 12

Twenty-five soft contact lenses made from polymacon (poly(2-hydroxyethylmethacrylate) crosslinked with ethyleneglycol dimethacrylate and swollen to 38% water) were coated with 250,000 MW PAA and were placed into a solution of 62.5 g bovine colostrum lactoferrin in 25 mL 0.10 molar pH 4.7 MES buffer to which 0.375 g EDC were added. After 18 hr of slow stirring at room temperature, these lactoferrin-coated lenses were rinsed ×10 with fresh borate buffered saline solution. Approximately 91 µg of lactoferrin were found on each lens by hydrolysis with 6 N HCl and derivitization with phenyl thioisocyanate followed by HPLC.

Example 13

Twelve soft contact lenses made from polymacon were placed into a 48 mL solution of 1.5% 60,000 MW poly (acrylic acid sodium salt) and 1.4% concentrated (35% by wt in water) HCl in borate buffered saline solution into which 0.144 g EDC were added. After 1 hr of rolling at room temperature, these lenses were rinsed ×10 with fresh borate buffered saline solution.

The lenses were then placed into a solution of 30 mg bovine colostrum lactoferrin in 12 mL 0.10 molar pH 47.7 MES buffer to which 0.18 g EDC were added. After 60 hr of rolling at room temperature, these lactoferrin coated lenses were rinsed ×10 with fresh borate buffered saline solution.

The lenses were then placed into 1.2 g solution of 5% NH$_4$Cl in DI water into which 2.4 g EDC were added. After 1 hr rolling at room temperature, the lenses were rinsed ×5 with fresh borate buffered saline solution. Approximately 151 µg of lactoferrin were found on each lens by hydrolysis with 6 N HCl and derivitization with phenyl thioisocyanate followed by HPLC.

Example 14

Forty etafilcon A lenses were placed into 120 mL solution of 1.20 g bovine albumin in DI water into which 0.60 g EDC were added. After 65 hr of rolling at room temperature, the lenses were rinsed ×10 in fresh borate buffered saline solution. Approximately 6 μg of albumin were found on each lens by hydrolysis with 6 N HCl and derivitization with phenyl thioisocyanate followed by HPLC.

Example 15

Soft, hydrogel contact lenses made by the procedure of Example 3 were coated with 250,000 MW PAA as follows. 10 lenses were placed into 30 mL of 3 wt percent PAA solution in borate buffered saline. 0.09 g EDC were added and after 1 hr, the lenses were rinsed ×5 with fresh borate buffered saline solution. Seven of the PAA-coated lenses were immersed in 10 mL of pH 6.05 MES buffer containing 2.88 g of XTJ-506 Jeffamine, the product of a reaction of a monohydric alcohol initiator with ethylene and propylene glycol in a ratio of 19:3, followed by conversion of the resulting terminal hydroxyl group to an amine (MW approximately 1000). 0.6 g EDC were added and, after 5.5 hr at room temperature, the lenses were rinsed ×4 with fresh borate buffered saline solution. The lenses were treated with rhodamine using the procedure of Example 3. The lenses exhibited less red color compared to PAA-coated lenses untreated with XTJ-506 Jeffamine. The lenses had an advancing contact angle in packing solution of 66 and receding angle of 48 degrees with buffered saline.

Example 16

Contact lenses were made by copolymerizing DMA and TRIS with the reaction product of 1 mole of 5,000 MW bisaminopropylpolydimethylsiloxane with 4 moles glycidyl methacrylate. One of the lenses was placed into a 1 wt percent solution of EDC in water for 5 min. The lens was then placed into 2 mL of a solution of 3 wt percent PAA (MW 250,000) for 1 hr. A very slight amount of precipitate was observed in the solution. The lens was evaluated by AFM and found to have a uniform coating.

Examples 17–24

Silicone lenses were made and soaked in EDC and PAA (MW 250,000) as in Example 16 at the times and temperatures indicated in Table 3.

TABLE 3

| Example | EDC | Time in EDC (min) | PAA | Precipitate | Coating Quality | Advancing Contact Angle |
|---|---|---|---|---|---|---|
| 17 | 1.0% | 5 | 3.0% | Very slight | Good | — |
| 18 | 1.0% | 10 | 3.0% | Very slight | Good | 34.8 |
| 19 | 1.0% | 15 | 3.0% | Very Slight | Good | 50.1 |
| 20 | 5.0% | 1 | 3.0% | Yes | Good | — |
| 21 | 5.0% | 10 | 3.0% | Yes | Good | 38.6 |
| 22 | 5.0% | 15 | 3.0% | Yes | Good | 36.6 |
| 23 | 1.0% | 5 | 8.0% | No | Good | 43.1 |
| 24 | 1.0% | 15 | 8.0% | No | Good | 38.1 |

The results indicate that a good coating was produced.

Examples 25–31

The uncoated silicone lenses of Example 16 were soaked in EDC and then 250,00 MW PAA. The times, concentrations and results are shown on Table 4. Coating quality was evaluated by treatment with rhodamine as in Example 3.

TABLE 4

| Example | EDC | Time in EDC (min) | PAA | Time in PAA (min) | Coating Quality | Precipitate |
|---|---|---|---|---|---|---|
| 25 | 1.0% | 5 | 3.0% | 60 | Good | Very slight |
| 26 | 1.0% | 10 | 3.0% | 60 | Good | Very slight |
| 27 | 1.0% | 15 | 3.0% | 60 | Good | Very Slight |
| 28 | 0.5% | 5 | 3.0% | 60 | — | No |
| 29 | 0.5% | 10 | 3.0% | 60 | — | No |
| 30 | 0.5% | 15 | 3.0% | 60 | — | No |
| 31 | 1.0% | 5 | 8.0% | 60 | Good | No |

Examples 32–36

Lenses were made as in Example 16 and soaked in EDC and then PAA (250,000 MW). The times, concentrations and results are shown on Table 5. Coating quality was evaluated by treatment with rhodamine as in Example 3.

TABLE 5

| Example | EDC | Time in EDC (min) | PAA | Time in PAA (min) | Coating Quality | Precipitate |
|---|---|---|---|---|---|---|
| 32 | 2.0% | 10 | 3.0% | 60 | Good | Moderate |
| 33 | 1.0% | 10 | 3.0% | 60 | Good | Slight |
| 34 | 0.50% | 10 | 3.0% | 60 | Good | Very Slight |
| 35 | 0.25% | 10 | 3.0% | 60 | Good | No |
| 36 | 0.13% | 10 | 3.0% | 60 | Good | No |

The results demonstrate that good coatings were produced.

Examples 37–45

Lenses made as in Example 3 were soaked in EDC and PAA (MW 250,000). The times, concentrations and results are shown on Table 6. Coating quality was evaluated by treatment with rhodamine as in Example 3.

TABLE 6

| Example | EDC | Time in EDC (min) | PAA | Time in PAA (min) | Coating Quality |
|---|---|---|---|---|---|
| 37 | 0.50% | 10 | 3.0% | 0 | None |
| 38 | 0.50% | 10 | 3.0% | 10 | Slight |
| 39 | 0.50% | 10 | 3.0% | 50 | Good |
| 40 | 0.50% | 10 | 3.0% | 60 | Good |
| 41 | 0.50% | 10 | 3.0% | 1000 | Good |
| 42 | 0.50% | 10 | 0.5% | 60 | Good |
| 43 | 0.50% | 10 | 1.0% | 60 | Good |
| 44 | 0.50% | 10 | 3.0% | 60 | Good |
| 45 | 0.50% | 10 | 6.0% | 60 | Good |

The results of Examples 37–41 indicate that with the demonstrated levels of EDC, approximately 10 or more minutes in the PAA is desirable. Examples 42–45 illustrate that the concentration of PAA may be varied.

Examples 46–50

In each example three lenses as described in Example 3, coated with PAA, were placed into solutions of 6.0 ml water containing $NH_4Cl$ levels given in Table 7. EDC was added, and the vials were rolled for three hours. The lenses were then treated with rhodamine as described in Example 3.

TABLE 7

| Example | NH₄Cl (g) | EDC (g) | Rhodamine |
|---|---|---|---|
| 46 | 0.006 | 0.012 | Very faint |
| 47 | 0.03 | 0.060 | Very faint |
| 48 | 0.06 | 0.12 | Very faint |
| 49 | 0.12 | 0.30 | Very faint |
| 50 | 0.30 | 0.60 | Very faint |
| Untreated control | 0 | 0 | Red |

These results indicate that the amount of EDC and NH₄Cl can be varied over a wide range and still produce essentially complete conversion of carboxyl groups to amide groups.

What is claimed is:

1. A method for manufacturing biomedical devices comprising the step of contacting at least one surface of a biomedical device, the surface comprising an effective amount of carboxyl groups, with a coating-effective amount of an amine and a coupling effective amount of at least one coupling agent at a temperature of about 0 to about 95° C. and for a time of about 1 to about 360 minutes to produce a stable, amide-containing coating on the surface.

2. The method of claim 1, wherein the device is a contact lens.

3. The method of claim 1 or 2, wherein the amount of carboxyl groups is about 0.65 to about 65 nMol/cm².

4. The method of claim 1 or 2, wherein the coupling agent is selected from the group consisting of a carbodiimide., acid halide of an inorganic or organic acid, isocyanide, N,N'-carbonyldiimidazole and combinations thereof.

5. The method of claim 4, wherein the coupling agent is a carbodiimide.

6. The method of claim 5, wherein the carbodiimide is 1-ethyl-3-(3-dimethylaminopropyl) carbodiimide or dicyclohexyl carbodiimide.

7. The method of claim 1 or 2, wherein the amine is selected from the group consisting of a primary amine, a secondary amine, an acid salt of a primary or secondary amine, an amine-containing protein, an amine-containing antibiotic, and combinations thereof.

8. The method of claim 1 or 2, wherein the amine is selected from the group consisting of ammonium chloride, glucosamine hydrochloride, dimethylamine hydrochloride, ethanolamine hydrochloride, diethanolamine hydrochloride, polyethylene glycol amines, lactoferrin, lysozyme, albumin, casein, cytochrome C, immunoglobulins, avidin, heparin, polymyxin, and combinations thereof.

9. The method of claim 1 or 2, wherein the stable, amide-containing coating produced is a polyacrylamide or a polymethacrylamide coating.

10. A method for manufacturing biomedical devices comprising the steps of: a.) coating at least one surface of a device with one or more carboxyl functional polymers; and b.) contacting the at least one surface with a coating-effective amount of an amine and a coupling effective amount of at least one coupling agent at a temperature of about 0 to about 95° C. and for a time of about 1 to about 360 minutes to produce a stable, amide-containing coating on the surface.

11. The method of claim 10, wherein the device is a contact lens.

12. The method of claim 10 or 11 wherein the one or more carboxyl functional polymer is selected from the group consisting of poly(acrylic acid), poly(methacrylic acid), poly(maleic acid), poly(itaconic acid), block or random copolymers of (meth)acrylic acid, acrylic acid, maleic acid, itaconic acid with any reactive vinyl monomer, carboxymethylated polymers, , and mixtures thereof.

13. The method of claim 10 or 11, wherein the carboxyl functional polymer is poly(acrylic acid).

14. The method of claim 10 or 11, wherein the coupling agent is selected from the group consisting of a carbodiimide, acid halide of an inorganic or organic acid, isocyanide, and combinations thereof.

15. The method of claim 10 or 11, wherein the coupling agent is a carbodiimide.

16. The method of claim 15, wherein the carbodiimide is 1-ethyl-3-(3-dimethylaminopropyl) carbodiimide or dicyclohexyl carbodiimide.

17. The method of claim 10 or 11, wherein the amine is selected from the group consisting of a primary amine, a secondary amine, an acid salt of a primary or secondary amine, an amine-containing protein, an amine-containing antibiotic, and combinations thereof.

18. The method of claim 10 or 11, wherein the amine is selected from the group consisting of ammonium chloride, glucosamine hydrochloride, dimethylamine hydrochloride, polyethylene glycol amines, lactoferrin, lysozyme, albumin, casein, cytochrome C, immunoglobulins, avidin, heparin, polymyxin, and combinations thereof.

19. The method of claim 10, wherein step a.) is carried out by: (i.) contacting the at least one surface with a coupling effective amount of a coupling agent for about 0.5 to about 60 minutes; and (ii.) contacting, subsequently, the at least one surface with a carboxyl functional polymer for a period of about 1 to about 1000 minutes to coat the at least one surface with the carboxyl functional polymer.

20. The method of claim 19, wherein the coupling agent is selected from the group consisting of a carbodiimide, acid halide of an inorganic or organic acid, isocyanide, and combinations thereof.

21. The method of claim 20, wherein the coupling agent is a carbodiimide.

22. The method of claim 21, wherein the carbodiimide is 1-ethyl-3-(3-dimethylaminopropyl) carbodiimide.

23. The method of claim 19, wherein the carboxyl functional polymer is selected from the group consisting of poly(acrylic acid), poly(methacrylic acid), poly(maleic acid), poly(itaconic acid), block or random copolymers of (meth)acrylic acid, acrylic acid, maleic acid, itaconic acid with any reactive vinyl monomer, carboxymethylated polymers, and mixtures thereof.

24. The method of claim 23, wherein the carboxyl functional polymer is poly(acrylic acid).

25. The method of claim 24, wherein the coupling agent is a carbodiimide.

26. The method of claim 25, wherein the carbodiimide is 1-ethyl-3-(3-dimethylaminopropyl) carbodiimide.

27. The method of claim 24, wherein the amine is selected from the group consisting of a primary amine, a secondary amine, an acid salt of a primary or secondary amine, an amine-containing protein, an amine-containing antibiotic, and combinations thereof.

28. The method of claim 27, wherein the amine is lactoferrin.

29. A contact lens comprising at least one surface having an amide-containing coating coupled thereto by at least one coupling agent.

30. The lens of claim 29, wherein the amide-containing coating is a coating formed from at least one amine selected from the group consisting of ammonium chloride, glucosamine hydrochloride, dimethylamine hydrochloride, ethanolamine hydrochloride, diethanolamine hydrochloride, polyethylene glycol amines, lactoferrin, lysozyme, albumin, casein, cytochrome C, immunoglobulins, avidin, heparin, polymyxin, and combinations thereof.

31. The lens of claim 29, wherein the amide-containing coating is a polyacrylamide coating.

* * * * *